(12) United States Patent
De Villiers-Zur Hausen et al.

(10) Patent No.: US 6,589,532 B1
(45) Date of Patent: Jul. 8, 2003

(54) PAPILLOMA VIRUSES, MEANS FOR THE DETECTION THEREOF AND THERAPY FOR DISEASES CAUSED THEREBY

(75) Inventors: Ethel-Michele De Villiers-Zur Hausen, Wald-Michelbach (DE); Harald Zur Hausen, Wald-Michelbach (DE)

(73) Assignee: Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/786,454

(22) PCT Filed: Sep. 1, 1999

(86) PCT No.: PCT/DE99/02824
§ 371 (c)(1),
(2), (4) Date: Jul. 12, 2001

(87) PCT Pub. No.: WO00/14112
PCT Pub. Date: Mar. 16, 2000

(30) Foreign Application Priority Data

Sep. 3, 1998 (DE) .......................................... 198 40 263

(51) Int. Cl.⁷ ........................ A61K 39/12; C12N 15/09
(52) U.S. Cl. ............................... 424/204.1; 424/199.1; 435/69.3; 435/69.1; 435/320.1; 435/252.3; 530/300; 530/350; 530/403; 536/23.72
(58) Field of Search .......................... 424/204.1, 194.1; 435/69.3, 69.1, 320.1, 252.3; 530/350, 403, 300; 536/23.72

(56) References Cited

FOREIGN PATENT DOCUMENTS

| DE | 197 35 118 C | 8/1998 |
|---|---|---|
| WO | WO 95/30754 A | 11/1995 |
| WO | WO 96/30520 A | 10/1996 |

OTHER PUBLICATIONS

Delius et al. Current Topics in Microbiology and Immunology, (1994) 186 13–31.*

Bernard et al., 1994, "Identification and assessment of known and novel human papillomaviruses by polymerase chain reaction amplification, restriction fragment length polymorphisms, nucleotide sequence, and phylogenetic algorithms," *J. Infect. Dis.* 170:1077–1085.

Database EMBL 'Online!, Nov. 26, 1994, "Human papillomavirus isolate CP8304 L1 protein gene, My09/My11 region, partial cds" Accession No. U12480.

Database EMBL 'Online!, Dec. 31, 1994, "Human papillomavirus type 62," Accession No. U12499.

Database SWISSPROT, Oct. 1, 1996, "Major capsid protein L1," Accession No. P50823.

Database SPTREMBL, Nov. 1, 1996, "L1 protein," Accession No. Q84235.

Delius et al., 1998, "The genomes of three of four novel HPV types, defined by differences of their L1 genes, show high conservation of the E7 gene and the URR," *Virology* 240(2):359–365.

Firzlaff et al., 1988, "Detection of human papillomavirus capsid antigens in various squamous epithelial lesions using antibodies directed against the L1 and L2 open reading frames," *Virology* 164:467–477.

Hagensee et al., 1993, "Self–assembly of human papillomavirus type 1 capsids by expression of the L1 protein alone or by coexpression of the L1 and L2 capsid proteins," *J. Virol.* 67(1):315–322.

Kirnbauer et al., 1993, "Efficient self–assembly of human papillomavirus type 16 L1 and L2 into virus–like particles," *J. Virol.* 67(12):6929–6936.

Peyton and Wheeler, 1994, "Identification of five novel human papillomavirus sequences in the New Mexico triethnic population," *J. Infect. Dis.* 170:1089–1092.

zur Hausen, 1977, "Human papiloomaviruses and their possible role in squamous cell carcinomas," *Curr. Top. Microbiol. Immunol.* 78:1–30.

zur Hausen, 1996, "Papillomavirus infections—a major cause of human cancers," *Biochim Biophys Acta* 1288(2):F55–F78.

* cited by examiner

*Primary Examiner*—Ali R. Salimi
(74) *Attorney, Agent, or Firm*—Pennie & Edmonds LLP

(57) ABSTRACT

The invention relates to DNA coding for a peptide of a papilloma virus major capsid protein or a papilloma virus genome. The invention also relates to proteins coded by the papilloma virus genome and antibodies directed against said proteins, in addition to the use thereof in diagnosis, therapy and vaccination.

16 Claims, 6 Drawing Sheets

DL416.seq   from: 1 to: 425

```
        N   Q   M   F   V   T   V   V   D   T   T   R   S   T   N   F   T   I   C   T   -
      AATCAAATGTTTGTTACTGTGGTGGATACTACTAGGAGTACTAATTTTACTATTTGTACC
   1  ------------+---------+---------+---------+---------+---------+  60
      TTAGTTTACAAACAATGACACCACCTATGATGATCCTCATGATTAAAATGATAAACATGG

A   S   T   A   A   A   E   Y   K   A   T   N   F   R   E   F   L   R   H   T   -
      GCCTCCACTGCTGCAGCAGAATACAAGGCTACCAACTTTAGGGAATTTTTGCGACACACG
  61  ------------+---------+---------+---------+---------+---------+ 120
      CGGAGGTGACGACGTCGTCTTATGTTCCGATGGTTGAAATCCCTTAAAAACGCTGTGTGC

E   E   F   D   L   Q   F   I   F   Q   L   C   K   I   Q   L   T   P   E   I   -
      GAGGAATTTGATTTGCAATTTATATTTCAATTGTGCAAAATACAGTTAACCCCCGAAATC
 121  ------------+---------+---------+---------+---------+---------+ 180
      CTCCTTAAACTAAACGTTAAATATAAAGTTAACACGTTTTATGTCAATTGGGGGCTTTAG

M   A   Y   L   H   N   M   N   K   D   L   L   D   D   W   N   F   G   V   L   -
      ATGGCCTACCTGCATAATATGAACAAGGACCTTTTGGATGACTGGAACTTTGGGGTTTTA
 181  ------------+---------+---------+---------+---------+---------+ 240
      TACCGGATGGACGTATTATACTTGTTCCTGGAAAACCTACTGACCTTGAAACCCCAAAAT

P   P   P   S   T   S   L   D   E   T   Y   H   Y   L   Q   S   R   A   I   T   -
      CCTCCCCCTTCCACTAGTTTAGATGAGACATATCACTATTTGCAGTCACGGGCTATTACA
 241  ------------+---------+---------+---------+---------+---------+ 300
      GGAGGGGGAAGGTGATCAAATCTACTCTGTATAGTGATAAACGTCAGTGCCCGATAATGT

C   Q   K   G   A   A   S   P   S   P   K   V   D   P   Y   A   Q   M   T   F   -
      TGTCAAAAGGGGCTGCTTCCCCGTCCCCCAAGGTGGACCCGTATGCGCAAATGACATTT
 301  ------------+---------+---------+---------+---------+---------+ 360
      ACAGTTTTCCCCCGACGAAGGGGCAGGGGGTTCCACCTGGGCATACGCGTTTACTGTAAA

W   T   V   D   L   K   D   K   L   S   T   D   L   D   Q   Y   S   L   G   R   -
      TGGACTGTGGATCTTAAGGACAAGTTGTCTACTGATTTGGATCAATATTCTCTAGGACGA
 361  ------------+---------+---------+---------+---------+---------+ 420
      ACCTGACACCTAGAATTCCTGTTCAACAGATGACTAAACCTAGTTATAAGAGATCCTGCT

K   -
      AAATT
 421  ----- 425
      TTTAA
```

Fig. 1

DL428.seq from: 1 to: 380

```
    AATCAGATGTTTATTACAGTTGCAGACAATACACGTAACACTAATTTTACTATTAGTGTG
  1 ---------+---------+---------+---------+---------+---------+ 60
    TTAGTCTACAAATAATGTCAACGTCTGTTATGTGCATTGTGATTAAAATGATAATCACAC

N  Q  M  F  I  T  V  A  D  N  T  R  N  T  N  F  T  I  S  V  -

TCCACGGAGGCCGCTCAGACTGAGGAATATAATGCAAACAATATTAGAGAGTATTTAAGA
 61 ---------+---------+---------+---------+---------+---------+ 120
    AGGTGCCTCCGGCGAGTCTGACTCCTTATATTACGTTTGTTATAATCTCTCATAAATTCT

S  T  E  A  A  Q  T  E  E  Y  N  A  N  N  I  R  E  Y  L  R  -

CATGTAGAAGAGTATCAAATTTCATTAATCTTACAGTTGTGTAAAGTACCTTTGGTAGCA
121 ---------+---------+---------+---------+---------+---------+ 180
    GTACATCTTCTCATAGTTTAAAGTAATTAGAATGTCAACACATTTCATGGAAACCATCGT

H  V  E  E  Y  Q  I  S  L  I  L  Q  L  C  K  V  P  L  V  A  -

GAAGTATTATCCCAGATTAATGCAATGAATTCAGGCATATTAGAAGAGTGGCAATTAGGG
181 ---------+---------+---------+---------+---------+---------+ 240
    CTTCATAATAGGGTCTAATTACGTTACTTAAGTCCGTATAATCTTCTCACCGTTAATCCC

E  V  L  S  Q  I  N  A  M  N  S  G  I  L  E  E  W  Q  L  G  -

TTTGTTCCAACTCCTGAAAATGCTGTTCACGATATTTATAGATATATTGATTCAAAGGCC
241 ---------+---------+---------+---------+---------+---------+ 300
    AAACAAGGTTGAGGACTTTTACGACAAGTGCTATAAATATCTATATAACTAAGTTTCCGG

F  V  P  T  P  E  N  A  V  H  D  I  Y  R  Y  I  D  S  K  A  -

ACAAAATGCCCAGATGCTGTTGAGCCCACAGAAAAAGAAGATCCCTTTGCTAAATACTCA
301 ---------+---------+---------+---------+---------+---------+ 360
    TGTTTTACGGGTCTACGACAACTCGGGTGTCTTTTTCTTCTAGGGAAACGATTTATGAGT

T  K  C  P  D  A  V  E  P  T  E  K  E  D  P  F  A  K  Y  S  -

TTTTGGAATGTTGATCTAAC
361 ---------+---------+ 380
    AAAACCTTACAACTAGATTG

DL436.seq    from: 1 to: 377

```
     AATCAACTGTTTATTACTGTAGCAGATAATACCAGAAACACAAATTTTACTATAAGCGTA
  1  ---------+---------+---------+---------+---------+---------+  60
     TTAGTTGACAAATAATGACATCGTCTATTATGGTCTTTGTGTTTAAAATGATATTCGCAT

N  Q  L  F  I  T  V  A  D  N  T  R  N  T  N  F  T  I  S  V   -

TCCACAGAAGCTGATGCACAGCAATATAATGCTAGTAACATTAGAGAATATCTAAGACAT
 61  ---------+---------+---------+---------+---------+---------+  120
     AGGTGTCTTCGACTACGTGTCGTTATATTACGATCATTGTAATCTCTTATAGATTCTGTA

S  T  E  A  D  A  Q  Q  Y  N  A  S  N  I  R  E  Y  L  R  H   -

GTAGAAGAATATCAACTGTCTTTGATTCTTCAATTATGCAAAGTTTCTTTGGTTCCAGAA
121  ---------+---------+---------+---------+---------+---------+  180
     CATCTTCTTATAGTTGACAGAAACTAAGAAGTTAATACGTTTCAAAGAAACCAAGGTCTT

V  E  E  Y  Q  L  S  L  I  L  Q  L  C  K  V  S  L  V  P  E   -

GTTTTATCTCAAATTAATGCAATGAATTCGAATATTTTGGAAGATTGGCAATTAGGATTT
181  ---------+---------+---------+---------+---------+---------+  240
     CAAAATAGAGTTTAATTACGTTACTTAAGCTTATAAAACCTTCTAACCGTTAATCCTAAA

V  L  S  Q  I  N  A  M  N  S  N  I  L  E  D  W  Q  L  G  F   -

GTACCAACACCAGATAATTCTGTGCATGACACATATAGATATATTAATTCAAAGGCTACT
241  ---------+---------+---------+---------+---------+---------+  300
     CATGGTTGTGGTCTATTAAGACACGTACTGTGTATATCTATATAATTAAGTTTCCGATGA

V  P  T  P  D  N  S  V  H  D  T  Y  R  Y  I  N  S  K  A  T   -

AAATGTCCAGATGCTGTAGAACCTAAAGAAAGAAAGAATCCATTTGCTAAATATACATTT
301  ---------+---------+---------+---------+---------+---------+  360
     TTTACAGGTCTACGACATCTTGGATTTCTTTCTTTCTTAGGTAAACGATTTATATGTAAA

K  C  P  D  A  V  E  P  K  E  R  K  N  P  F  A  K  Y  T  F   -

TGGGATGTTGATCTAAC
361  ---------+-------  377
     ACCCTACAACTAGATTG

DL473.seq from: 1 to: 380

```
    AATCAGATGTTTATTACTGTAGCAGATAACACACGGAATACTAATTTTACCATTAGTGTT
  1 ---------+---------+---------+---------+---------+---------+ 60
    TTAGTCTACAAATAATGACATCGTCTATTGTGTGCCTTATGATTAAAATGGTAATCACAA

N  Q  M  F  I  T  V  A  D  N  T  R  N  T  N  F  T  I  S  V  -

ACCAGTGAAGATGTAAGCACTGCACAATATAATGCTCAAAATATTAGAGAGTATATGAGA
 61 ---------+---------+---------+---------+---------+---------+ 120
    TGGTCACTTCTACATTCGTGACGTGTTATATTACGAGTTTTATAATCTCTCATATACTCT

T  S  E  D  V  S  T  A  Q  Y  N  A  Q  N  I  R  E  Y  M  R  -

CATGTAGAAGAATATCAGCTATCTTTTATTTTGCAATTATGCAGAGTACCTTTAGAAGCT
121 ---------+---------+---------+---------+---------+---------+ 180
    GTACATCTTCTTATAGTCGATAGAAAATAAAACGTTAATACGTCTCATGGAAATCTTCGA

H  V  E  E  Y  Q  L  S  F  I  L  Q  L  C  R  V  P  L  E  A  -

GAGGTTTTAACACAAATTAATGCCATGAATTCTGGTATACTTGAAAATTGGCAACTGGGT
181 ---------+---------+---------+---------+---------+---------+ 240
    CTCCAAAATTGTGTTTAATTACGGTACTTAAGACCATATGAACTTTTAACCGTTGACCCA

E  V  L  T  Q  I  N  A  M  N  S  G  I  L  E  N  W  Q  L  G  -

TTTGTACCAGCTCCAGATAATGCAGTGCATGATACATATCGATATTTAAGTTCAAAAGCT
241 ---------+---------+---------+---------+---------+---------+ 300
    AAACATGGTCGAGGTCTATTACGTCACGTACTATGTATAGCTATAAATTCAAGTTTTCGA

F  V  P  A  P  D  N  A  V  H  D  T  Y  R  Y  L  S  S  K  A  -

ACAAAGTGTCCTGATGCAGTTCAAGAAACAGAAAAAGAAGACCCCTTTGGAAAATATACA
301 ---------+---------+---------+---------+---------+---------+ 360
    TGTTTCACAGGACTACGTCAAGTTCTTTGTCTTTTTCTTCTGGGGAAACCTTTTATATGT

T  K  C  P  D  A  V  Q  E  T  E  K  E  D  P  F  G  K  Y  T  -

TTCTGGGATGTAGATCTAAC
361 ---------+---------+ 380
    AAGACCCTACATCTAGATTG

KG80.seq    from: 1 to: 389

```
      GATAGATCTACATTCCAAAAGTTTAATTTTGCATAGGGGTCGGGCCGTTCCTTTGGAGGA
  1   ---------+---------+---------+---------+---------+---------+  60
      CTATCTAGATGTAAGGTTTTCAAATTAAAACGTATCCCCAGCCCGGCAAGGAAACCTCCT

L  D  V  N  W  F  N  L  K  A  Y  P  D  P  R  E  K  P  P  -

TTCTTATCAGGACACCTTGTGGCTAAAGACTCAATAAATCTATATGTATCGTGTATGGGG
 61   ---------+---------+---------+---------+---------+---------+ 120
      AAGAATAGTCCTGTGGAACACCGATTTCTGAGTTATTTAGATATACATAGCACATACCCC

N  K  D  P  C  R  T  A  L  S  E  I  F  R  Y  T  D  H  I  P  -

TTATCAGGAGTTGGAACAAAGCCCAACTGCCAATCCTCTAATATATTGGAGTTCATGGCA
121   ---------+---------+---------+---------+---------+---------+ 180
      AATAGTCCTCAACCTTGTTTCGGGTTGACGGTTAGGAGATTATATAACCTCAAGTACCGT

N  D  P  T  P  V  F  G  L  Q  W  D  E  L  I  N  S  N  M  A  -

TTGATCTGTGCAAGAACCTCTGCCTTTAAAGGAATTTTACATAGCTGTAAAATGAGAGAA
181   ---------+---------+---------+---------+---------+---------+ 240
      AACTAGACACGTTCTTGGAGACGGAAATTTCCTTAAAATGTATCGACATTTTACTCTCTT

N  I  Q  A  L  V  E  A  K  L  P  I  K  C  L  Q  L  I  L  S  -

ATTTCGTATTCTTCTACATGCCTTAAATATTCTCTGAATTGTGTGGCCTTGTAGTTTTGA
241   ---------+---------+---------+---------+---------+---------+ 300
      TAAAGCATAAGAAGATGTACGGAATTTATAAGAGACTTAACACACCGGAACATCAAAACT

I  E  Y  E  E  V  H  R  L  Y  E  R  F  Q  T  A  K  Y  N  Q  -

ATATCCTTTATATTCCCTCCTTCACTATATATGGATATACTGAAGTTAGTGTTTCGCGTG
301   ---------+---------+---------+---------+---------+---------+ 360
      TATAGGAAATATAAGGGAGGAAGTGATATATACCTATATGACTTCAATCACAAAGCGCAC

I  D  K  I  N  G  G  E  S  Y  I  S  I  S  F  N  T  N  R  T  -

TTGTCTACAACAGTAATAAACAGCTGATT
361   ---------+---------+--------- 389
      AACAGATGTTGTCATTATTTGTCGACTAA

```
tn111.seq   from: 1 to: 422

ATAGAAGACGGGGATATGGCAGACATTGGATATGGTAATATTAATTTTAAAACCTTACAA
    1  ------------+---------+---------+---------+---------+---------+  60
       TATCTTCTGCCCCTATACCGTCTGTAACCTATACCATTATAATTAAAATTTTGGAATGTT

I  E  D  G  D  M  A  D  I  G  Y  G  N  I  N  F  K  T  L  Q    -

CAAAACAGATCTGATGTCAGTTTAGATATAGTTGACGAAATTTGCAAGTATCCTGATTTT
   61  ------------+---------+---------+---------+---------+---------+  120
       GTTTTGTCTAGACTACAGTCAAATCTATATCAACTGCTTTAAACGTTCATAGGACTAAAA

Q  N  R  S  D  V  S  L  D  I  V  D  E  I  C  K  Y  P  D  F    -

TTGAAAATGCAAAATAATATTTATGGAGATGCTTGCTTTTTTTATGCTAGACGGGAGCAA
  121  ------------+---------+---------+---------+---------+---------+  180
       AACTTTTACGTTTTATTATAAATACCTCTACGAACGAAAAAAATACGATCTGCCCTCGTT

L  K  M  Q  N  N  I  Y  G  D  A  C  F  F  Y  A  R  R  E  Q    -

TGTTATGCTAGACATTTTTTTGTACGAGGAGGAAAACCAGGTGACGACATTCCTGCATCT
  181  ------------+---------+---------+---------+---------+---------+  240
       ACAATACGATCTGTAAAAAAACATGCTCCTCCTTTTGGTCCACTGCTGTAAGGACGTAGA

C  Y  A  R  H  F  F  V  R  G  G  K  P  G  D  D  I  P  A  S    -

CAGATAGATGATGGCAATTTAAAAAATGAATATTACATTCCTGCTGACTCAGCGCAGCCA
  241  ------------+---------+---------+---------+---------+---------+  300
       GTCTATCTACTACCGTTAAATTTTTTACTTATAATGTAAGGACGACTGAGTCGCGTCGGT

Q  I  D  D  G  N  L  K  N  E  Y  Y  I  P  A  D  S  A  Q  P    -

CAAAACAAACTTGGAAATTCCATGTATTTCCCAACTATAAGTGGTTCATTGGTGTCAAGT
  301  ------------+---------+---------+---------+---------+---------+  360
       GTTTTGTTTGAACCTTTAAGGTACATAAAGGGTTGATATTCACCAAGTAACCACAGTTCA

Q  N  K  L  G  N  S  M  Y  F  P  T  I  S  G  S  L  V  S  S    -

GATGCCCAATTATTTAACAGGCCCTTCTGGCTACAAAGAGCACAAGGCCACAACAACGGG
  361  ------------+---------+---------+---------+---------+---------+  420
       CTACGGGTTAATAAATTGTCCGGGAAGACCGATGTTTCTCGTGTTCCGGTGTTGTTGCCC

PAPILLOMA VIRUSES, MEANS FOR THE DETECTION THEREOF AND THERAPY FOR DISEASES CAUSED THEREBY

This is a national phase filing of the Application No. PCT/DE99/02824, which was filed with the Patent Corporation Treaty on Sep. 1, 1999, and is entitled to priority of the German Patent Application 198 40 263.5, filed Sep. 3, 1998.

FIELD OF THE INVENTION

This invention relates to a DNA coding for a peptide of a papilloma virus major capsid protein or a papilloma virus genome. This invention also relates to proteins coded by the papilloma virus genome and antibodies directed against them as well as their use in diagnosis, therapy and vaccination.

BACKGROUND OF THE INVENTION

It is known that papilloma viruses infect the epithelium of human beings and animals. Human papilloma viruses (hereinafter referred to as HP viruses) are found in benign epithelial neoplasms, e.g. warts, condylomas in the genital zone, and malignant epithelial neoplasms, e.g. carcinomas of the skin and the uterus (cf. Zu Hausen, H., Biochimica et Biophysica Acta (BBA) 1288, (1996), pp. 55–78). HP viruses are also considered for the growth of malignant tumors in the oropharyngeal zone (cf. Zur Hausen, H., Curr. Top. Microbiol. Immunol. 78, (1977), pp. 1–30).

Papilloma viruses have an icosahedral capsid without envelope in which a circular, double-stranded DNA molecule of about 7900 bp is present. The capsid comprises a major capsid protein (L1) and a minor capsid protein (L2). Both proteins, coexpressed or L1 expressed alone, result in vitro in the formation of virus-like particles (cf. Kirnbauer, R. et al., Journal of Virology, (1993), pp. 6929–6936).

Papilloma viruses cannot be proliferated in monolayer cell culture. Therefore, their characterization is extremely difficult, the detection of papilloma viruses already creating considerable problems. This applies particularly to papilloma viruses in carcinomas of the skin.

Thus, it is the object of the present invention to provide a product by which papilloma viruses can be detected, particularly in carcinomas of the skin. Furthermore, a product should be provided to be able to take therapeutic steps against these papilloma viruses.

According to the invention this is achieved by providing the subject matters in the claims.

SUMMARY OF THE INVENTION

Therefore, the subject matter of the invention relates to a DNA coding for a peptide of a papilloma virus major capsid protein (L1), the peptide comprising the amino acid sequence of FIG. 1, FIG. 2, FIG. 3, FIG. 4, FIG. 5, or FIG. 6 (SEQ ID NOS: 2, 4, 6, 8, 10 or 12, respectively) or an amino acid sequence differing therefrom by one or more amino acids.

A further subject matter of the invention relates to a DNA coding for a peptide of a papilloma virus major capsid protein, the DNA comprising the base sequence of FIG. 1, FIG. 2, FIG. 3, FIG. 4, FIG. 5, or FIG. 6, (SEQ ID NOS: 1, 3, 5, 7, 9, or 11, respectively) or a base sequence differing therefrom by one or more base pairs.

BRIEF DESCRIPTION OF THE DRAWINGS

FIG. 1 shows the base sequence and the amino acid sequence (SEQ ID NOS: 1 and 2, respectively), derived therefrom, of a DNA coding for a peptide of L1 of a papilloma virus. This DNA was deposited as plasmid DL416 with DSM (Deutsche Sammlung von Miroorganismen und Zellkulturen [German-type collection of microorganisms and cell cultures]) under DSM 12309 on Jul. 14, 1998.

FIG. 2 shows the base sequence and the amino acid sequence (SEQ ID NOS: 3 and 4, respectively), derived therefrom, of a DNA coding for a peptide of L1 of a papilloma virus. This DNA was deposited as plasmid DL428 with DSM under DSM 12310 on Jul. 14, 1998.

FIG. 3 shows the base sequence and the amino acid sequence (SEQ ID NOS: 5 and 6, respectively), derived therefrom, of a DNA coding for a peptide of L1 of a papilloma virus. This DNA was deposited as plasmid DL463 with DSM under DSM 12311 on Jul. 14, 1998.

FIG. 4 shows the base sequence and the amino acid sequence (SEQ ID NOS: 7 and 8, respectively), derived therefrom, of a DNA coding for a peptide of L1 of a papilloma virus. This DNA was deposited as plasmid DL473 with DSM under DSM 12312 on Jul. 14, 1998.

FIG. 5 shows the base sequence and the amino acid sequence (SEQ ID NOS: 9 and 10, respectively), derived therefrom, of a DNA coding for a peptide of L1 of a papilloma virus. This DNA was deposited as plasmid KG80 with DSM under DSM 12313 on Jul. 14, 1998.

FIG. 6 shows the base sequence and the amino acid sequence (SEQ ID NOS: 11 and 12, respectively), derived therefrom, of a DNA coding for a peptide of L1 of a papilloma virus. This DNA was deposited as plasmid TN111 with DSM under DSM 12314 on Jul. 14, 1998.

DETAILED DESCRIPTION OF THE INVENTION

The above DNA was compared with the DNA of known papilloma viruses. Sequence homology studies were carried out. A homology having less than 90% shows that a DNA according to the invention is a new HP virus. The DNAs according to the invention have the following sequence homologies with respect to known papilloma viruses:

DNA of FIG. 1: 78% with respect to HP virus 61
DNA of FIG. 2: 91% with respect to HP virus 9 (DL428)
DNA of FIG. 3: 77% with respect to HP virus 17
DNA of FIG. 4: 80% with respect to HP virus 15
DNA of FIG. 5: 77% with respect to HP virus 12
DNA of FIG. 6: 81% with respect to HP virus 12

As to the DNA of FIG. 2 it must be noted that here only part of the open reading frame was observed which is located in a highly conserved region. If the above definition which relates to the entire L1 reading frame is used as a basis, a total harmony of less than 90% has to be expected here as well.

According to the invention, the above DNA can be present in a vector and expression vector, respectively. A person skilled in the art is familiar with examples thereof. In the case of an expression vector for *E. coli* these are e.g. pGEMEX, pUC derivatives, pGEM-T and pGEX-2T. For the expression in yeast e.g. pY100 and Ycpad1 have to be mentioned, while for the expression in animal cells e.g. pKCR, pEF-BOS, cDM8 and pCEV4 have to be indicated.

The person skilled in the art knows suitable cells to express the above DNA present in an expression vector. Examples of such cells comprise the *E. coli* strains HB101, DH1, x1776, JM101, JM 109, and XL1-Blue, the yeast strain Saccharomyces cerevisiae and the animal cells L, NH-3T3, FM3A, CHO, Cos, Vero, and HeLa.

The person skilled in the art knows in which way the above DNA has to be inserted in an expression vector. He is also familiar with the fact that the above DNA can be inserted in connection with a DNA coding for another protein and peptide, respectively, so that the above DNA can be expressed in the form of a fusion protein.

A further subject matter of the invention relates to a papilloma virus genome which comprises the above DNA. The expression "papilloma virus genome" also comprises an incomplete genome, i.e. fragments of a papilloma virus genome, which comprise the above DNA. This may be e.g. a DNA coding for L1 or a portion thereof.

A common process can be used for the provision of the above papilloma virus genome. It is favorable to use a process which comprises the following processing steps:

(a) isolation of the total DNA from a biopsy of epithelial neoplasm, (b) hybridization of the total DNA of (a) with the above DNA so as to detect a papilloma virus genome included in the total DNA of (a), and (c) cloning of the total DNA of (a), containing the papilloma virus genome, in a vector and optionally subcloning the resulting clone, all processing steps originating from common DNA recombination technique.

As far as the isolation, hybridization and cloning of cell DNA is concerned, reference is made by way of supplement to Sambrook et al., Molecular Cloning, A Laboratory manual, second edition, Cold Spring Harbor Laboratory (1989).

The expression "epithelial neoplasm" comprises any neoplasms of epithelium in man and animal. Examples of such neoplasms are warts, condylomas in the genital zone and carcinomas of the (mucous membrane) skin. The latter are used preferably to isolate the above papilloma virus genome.

The expression "vector" comprises any vectors suitable for cloning chromosomal DNA and extrachromosomal DNA, respectively. Examples of such vectors are cosmids such as pWE15 and Super Cos1, and phages such as π-phages, e.g. λZAP expressvector, πZAPII vector and πgt10 vector. In the present case, λ-phages are used preferably. The above vectors are known and obtainable from the company of Stratagene.

Papilloma virus genomes according to the invention may be present in integrated form in chromosonal DNA or in extrachromosomal fashion. The person skilled in the art is familiar with processes serving the clarification thereof. He also knows processes serving for finding out the optimum restriction enzymes for cloning the papilloma virus genomes. He will orient himself by genomes of known papilloma viruses. In particular, the person skilled in the art will pay corresponding attention to the above-mentioned HP viruses.

The provision of a papilloma virus genome referred to as DL473-G is described by way of example. For this purpose, the total DNA is isolated from a biopsy of a squamous epithelial carcinoma, cleaved by BamnHI and separated electrophoretically in an agarose gel. The agarose gel is then subjected to a blotting method so as to transfer the DNA to a nitrocellulose membrane. It is inserted in a hybridization method in which the DNA of FIG. 4 is used as labeled sample, optionally in combination with a DNA of HP virus 15. Hybridization with the papilloma virus DNA present in the total DNA is obtained.

Moreover, the above total DNA cleaved by BamnHI is cloned a λ-phage. The corresponding clones, i.e. the clones containing the papilloma virus DNA are identified by hybridization with the DNA of FIG. 4, optionally in combination with a DNA of the HP virus 15. The insert of these clones is then subjected to a further cloning in a plasmid vector so as to obtain a clone which contains the papilloma virus genome DL473-G. The genome is confirmed by sequencing.

Further papilloma virus genomes are provided analogously. They are designated in accordance with the DNAs used for their provision, namely by: DL416-G, DL428-G, D1436-G, KG80-G or TN111-G.

A further subject matter of the invention relates to a protein which is coded by the above papilloma virus genome. Such a protein is e.g. a major capsid protein (L1) or a minor capsid protein (L2). An above protein is prepared as usual. The preparation of L1 and L2, respectively, of the papilloma virus genome DL473-G is described by way of example. For this purpose, the HP virus 15 related to the DNA of FIG. 4 is used. Its full sequence and the position of individual DNA regions coding for protein are known. These DNAs are identified on the papilloma virus genome DL473-G by parallel restriction cleavages of both genomes and subsequent hybridization with various fragments concerning the DNA encoding L1 and L2, respectively. They are confirmed by sequencing. The DNA coding for L1 is referred to as DL473-G-L1 DNA and the DNA coding for L2 is referred to as DL473-G-L2 DNA.

Furthermore, the DNA coding for L1 and L2, respectively, is inserted in an expression vector. Examples thereof are mentioned above for E. coli, yeast and animal cells. In particular, reference is made to the vector pGEX-2T as regards the expression in E. coli (cf. Kimbauer, R. et al., supra). Having inserted the DLA473-G-L1 DNA and DL473-G-L2 DNA, one obtains pGEX-2T-DL473-G-L1 and pGEX-2T-DL473-G-L2, respectively. After transforming E. coli, these expression vectors express a glutathione S transferase L1 fusion protein and glutathione S transferase L2 fusion protein, respectively. The proteins are purified as usual.

The bacculovirus system and vaccina virus system, respectively, is mentioned for a further expression of the above DNA encoding L1 and L2, respectively. Expression vectors usable for this purpose are e.g. pEV mod. And pSynwtVI⁻ for the bacculovirus system (cf. Kirnbauer, R. et al. supra). For the vaccinia virus system especially vectors with the vaccinia virus "early" (p7.5k) promoter and "late" (Psynth, p11K) promoter, respectively, have to be mentioned (cf. Hagensee, M., E. et al., Journal of Virology (1993), pp. 315–322). The bacculovirus system is preferred in the present case. Having inserted the above DNA encoding L1 and L2, respectively, in pEV mod., one obtains pEVmod.-DL473-G-L1 and pEVmod.-DL473-G-L2, respectively.

The former expression vector as such or both expression vectors jointly lead to the formation of virus-like particles after injection of SF-9 insect cells. In the former case, such a particle comprises an L1 protein, while in the latter case it contains an L2 protein in addition to an L1 protein.

A virus-like particle of the latter case is also obtained by inserting the above DL473-G-L1 and DL473-G-L2 DNAs jointly in the expression vector pSynwtVI⁻ and using the resulting pSynwtVI⁻DL473-G-11/L2 for the infection of SF-9 insect cells. The above virus-like particles are purified as usual. They also represent a subject matter of the invention.

A further subject matter of the invention relates to an antibody directed against an above protein and virus-like particle, respectively. The preparation thereof is made as usual. It is described by way of example for the preparation of an antibody which is directed against a virus-like particle comprising an L1 of DL473-G. For this purpose, the virus-like particle is injected subcutaneously into BALB/c mice. This injection is repeated at intervals of 3 weeks each. About 2 weeks after the last injection, the serum containing the antibody is isolated and tested as usual.

In a preferred embodiment, the antibody is a monoclonal antibody. For its preparation, spleen cells are removed from the mice after the fourth injection and fused with myeloma cells as usual. The further cloning also takes place according to known methods.

By means of the present invention it is possible to detect papilloma viruses, particularly in carcinomas of the skin. For this purpose, the DNA according to the invention can be used as such or when comprised by a further DNA. The latter may also be a papilloma virus genome or a portion thereof.

The present invention also enables the provision of formerly unknown papilloma viruses. They are found especially in carcinomas of the skin. In addition, the invention supplies proteins and virus-like particles which originate from these papilloma viruses. Moreover, antibodies are provided which are directed against these proteins and particles, respectively.

The present invention also enables to take diagnostic and therapeutic steps in the case of papilloma virus diseases. Moreover, it supplies the possibility of building up a vaccine against papilloma virus infections. Thus, the present invention represents a break-through in the field of papilloma virus research.

The invention is explained by the examples.

EXAMPLES

Example 1

Identification of the Papilloma Virus Genome DL473-G

The total DNA is isolated from a biopsy of squamous cell carcinoma. 10 µg of the above DNA are cleaved by the restricted enzyme BamHI and separated electrophoretically in a 0.5% agarose gel. At the same time, 10 µg of the above DNA which was not cleaved is also separated. The agarose gel is subjected to a blotting method so as to transfer the DNA from the agarose gel to a nitrocellulose membrane. It is employed in a hybridization method in which the above DNA of FIG. 4 is used in combination with the HP virus-15 DNA as $p^{32}$-labeled sample. Hybridization with the blotted DNA is obtained.

The person skilled in the field of DNA recombination technique is familiar with the above methods. Reference is made to Sambrook et al., supra, by way of supplement.

Example 2

Cloning of the Papilloma Virus Genome DL473-G

The biopsy DNA obtained from Example 1 is cleaved by the restriction enzyme BamHI. The resulting fragments are used in a ligase reaction in which the dephosphorylated vector λZAP express cleaved by BamHI is also present. The resulting recombinant DNA molecules are packed in bacteriophages, and they are used for infecting bacteria. For these processing steps, the ZAP express vector kit offered by the company of Stratagene is used. The resulting phage plaques are then subjected to a hybridization process which uses the $p^{32}$-labeled HP virus-15 DNA. Hybridization with corresponding phage plaques is obtained. The BaniHI fragments of DL473-G are isolated therefrom and used in a further ligase reaction together with a BamHI-cleaved, dephosphorylated plasmid vector, pBluescript. The resulting recombinant DNA molecules are used for transforming bacteria, *E. coli* XL1-Blue. By restriction cleaves and hybridization with the above DNA samples, respectively, a bacterial clone containing the papilloma virus genome DL473-G is identified. The plasmid of this bacterial clone is referred to as pBlue-DL473-G.

SEQUENCE LISTING

<160> NUMBER OF SEQ ID NOS: 12

<210> SEQ ID NO 1
<211> LENGTH: 425
<212> TYPE: DNA
<213> ORGANISM: Papillomavirus sylvilagi
<220> FEATURE:
<221> NAME/KEY: CDS
<222> LOCATION: (1)..(423)

<400> SEQUENCE: 1

```
aat caa atg ttt gtt act gtg gtg gat act act agg agt act aat ttt      48
Asn Gln Met Phe Val Thr Val Val Asp Thr Thr Arg Ser Thr Asn Phe
1               5                   10                  15 act att tgt acc gcc tcc act gct gca gca gaa tac aag gct acc aac      96
Thr Ile Cys Thr Ala Ser Thr Ala Ala Ala Glu Tyr Lys Ala Thr Asn
            20                  25                  30 ttt agg gaa ttt ttg cga cac acg gag gaa ttt gat ttg caa ttt ata     144
Phe Arg Glu Phe Leu Arg His Thr Glu Glu Phe Asp Leu Gln Phe Ile
        35                  40                  45 ttt caa ttg tgc aaa ata cag tta acc ccc gaa atc atg gcc tac ctg     192
```

```
               Phe Gln Leu Cys Lys Ile Gln Leu Thr Pro Glu Ile Met Ala Tyr Leu
                50                  55                  60 cat aat atg aac aag gac ctt ttg gat gac tgg aac ttt ggg gtt tta         240
His Asn Met Asn Lys Asp Leu Leu Asp Asp Trp Asn Phe Gly Val Leu
 65                  70                  75                  80 cct ccc cct tcc act agt tta gat gag aca tgt cac tat ttg cag tca         288
Pro Pro Pro Ser Thr Ser Leu Asp Glu Thr Cys His Tyr Leu Gln Ser
                 85                  90                  95 cgg gct att aca tgt caa aag ggg gct gct tcc ccg tcc ccc aag gtg         336
Arg Ala Ile Thr Cys Gln Lys Gly Ala Ala Ser Pro Ser Pro Lys Val
            100                 105                 110 gac ccg tat gcg caa atg aca ttt tgg act gtg gat ctt aag gac aag         384
Asp Pro Tyr Ala Gln Met Thr Phe Trp Thr Val Asp Leu Lys Asp Lys
        115                 120                 125 ttg tct act gat ttg gat caa tat tct cta gga cga aaa tt                  425
Leu Ser Thr Asp Leu Asp Gln Tyr Ser Leu Gly Arg Lys
    130                 135                 140

<210> SEQ ID NO 2
<211> LENGTH: 141
<212> TYPE: PRT
<213> ORGANISM: Papillomavirus sylvilagi

<400> SEQUENCE: 2

Asn Gln Met Phe Val Thr Val Val Asp Thr Thr Arg Ser Thr Asn Phe
 1               5                  10                  15

Thr Ile Cys Thr Ala Ser Thr Ala Ala Glu Tyr Lys Ala Thr Asn
            20                  25                  30

Phe Arg Glu Phe Leu Arg His Thr Glu Glu Phe Asp Leu Gln Phe Ile
        35                  40                  45

Phe Gln Leu Cys Lys Ile Gln Leu Thr Pro Glu Ile Met Ala Tyr Leu
    50                  55                  60

His Asn Met Asn Lys Asp Leu Leu Asp Asp Trp Asn Phe Gly Val Leu
 65                  70                  75                  80

Pro Pro Pro Ser Thr Ser Leu Asp Glu Thr Cys His Tyr Leu Gln Ser
                 85                  90                  95

Arg Ala Ile Thr Cys Gln Lys Gly Ala Ala Ser Pro Ser Pro Lys Val
            100                 105                 110

Asp Pro Tyr Ala Gln Met Thr Phe Trp Thr Val Asp Leu Lys Asp Lys
        115                 120                 125

Leu Ser Thr Asp Leu Asp Gln Tyr Ser Leu Gly Arg Lys
    130                 135                 140

<210> SEQ ID NO 3
<211> LENGTH: 380
<212> TYPE: DNA
<213> ORGANISM: Papillomavirus sylvilagi
<220> FEATURE:
<221> NAME/KEY: CDS
<222> LOCATION: (1)..(378)

<400> SEQUENCE: 3 aat cag atg ttt att aca gtt gca gac aat aca cgt aac act aat ttt         48
Asn Gln Met Phe Ile Thr Val Ala Asp Asn Thr Arg Asn Thr Asn Phe
 1               5                  10                  15 act att agt gtg tcc acg gag gcc gct cag act gag gaa tat aat gca         96
Thr Ile Ser Val Ser Thr Glu Ala Ala Gln Thr Glu Glu Tyr Asn Ala
            20                  25                  30 aac aat att aga gag tat tta aga cat gta gaa gag tat caa att tca         144
Asn Asn Ile Arg Glu Tyr Leu Arg His Val Glu Glu Tyr Gln Ile Ser
```

-continued

```
              35                  40                  45
tta atc tta cag ttg tgt aaa gta cct ttg gta gca gaa gta tta tcc       192
Leu Ile Leu Gln Leu Cys Lys Val Pro Leu Val Ala Glu Val Leu Ser
         50                  55                  60 cag att aat gca atg aat tca ggc ata tta gaa gag tgg caa tta ggg       240
Gln Ile Asn Ala Met Asn Ser Gly Ile Leu Glu Glu Trp Gln Leu Gly
 65                  70                  75                  80 ttt gtt cca act cct gaa aat gct gtt cac gat att tat aga tat att       288
Phe Val Pro Thr Pro Glu Asn Ala Val His Asp Ile Tyr Arg Tyr Ile
                 85                  90                  95 gat tca aag gcc aca aaa tgc cca gat gct gtt gag ccc aca gaa aaa       336
Asp Ser Lys Ala Thr Lys Cys Pro Asp Ala Val Glu Pro Thr Glu Lys
            100                 105                 110 gaa gat ccc ttt gct aaa tac tca ttt tgg aat gtt gat cta ac            380
Glu Asp Pro Phe Ala Lys Tyr Ser Phe Trp Asn Val Asp Leu
        115                 120                 125
```

<210> SEQ ID NO 4
<211> LENGTH: 126
<212> TYPE: PRT
<213> ORGANISM: Papillomavirus sylvilagi

<400> SEQUENCE: 4

```
Asn Gln Met Phe Ile Thr Val Ala Asp Asn Thr Arg Asn Thr Asn Phe
 1               5                  10                  15

Thr Ile Ser Val Ser Thr Glu Ala Ala Gln Thr Glu Glu Tyr Asn Ala
            20                  25                  30

Asn Asn Ile Arg Glu Tyr Leu Arg His Val Glu Glu Tyr Gln Ile Ser
        35                  40                  45

Leu Ile Leu Gln Leu Cys Lys Val Pro Leu Val Ala Glu Val Leu Ser
     50                  55                  60

Gln Ile Asn Ala Met Asn Ser Gly Ile Leu Glu Glu Trp Gln Leu Gly
 65                  70                  75                  80

Phe Val Pro Thr Pro Glu Asn Ala Val His Asp Ile Tyr Arg Tyr Ile
                 85                  90                  95

Asp Ser Lys Ala Thr Lys Cys Pro Asp Ala Val Glu Pro Thr Glu Lys
            100                 105                 110

Glu Asp Pro Phe Ala Lys Tyr Ser Phe Trp Asn Val Asp Leu
        115                 120                 125
```

<210> SEQ ID NO 5
<211> LENGTH: 377
<212> TYPE: DNA
<213> ORGANISM: Papillomavirus sylvilagi
<220> FEATURE:
<221> NAME/KEY: CDS
<222> LOCATION: (1)..(375)

<400> SEQUENCE: 5

```
aat caa ctg ttt att act gta gca gat aat acc aga aac aca aat ttt       48
Asn Gln Leu Phe Ile Thr Val Ala Asp Asn Thr Arg Asn Thr Asn Phe
 1               5                  10                  15 act ata agc gta tcc aca gaa gct gat gca cag caa tat aat gct agt       96
Thr Ile Ser Val Ser Thr Glu Ala Asp Ala Gln Gln Tyr Asn Ala Ser
            20                  25                  30 aac att aga gaa tat cta aga cat gta gaa gaa tat caa ctg tct ttg       144
Asn Ile Arg Glu Tyr Leu Arg His Val Glu Glu Tyr Gln Leu Ser Leu
        35                  40                  45 att ctt caa tta tgc aaa ctt tgt ttg gtt cca gaa gtt tta tct caa       192
Ile Leu Gln Leu Cys Lys Leu Cys Leu Val Pro Glu Val Leu Ser Gln
```

```
                  50                   55                    60
att aat gca atg aat tcg aat att ttg gaa gat tgg caa tta gga ttt     240
Ile Asn Ala Met Asn Ser Asn Ile Leu Glu Asp Trp Gln Leu Gly Phe
65                   70                   75                   80 gta cca aca cca gat aat tct gtg cat gac aca tat aga tat att aat     288
Val Pro Thr Pro Asp Asn Ser Val His Asp Thr Tyr Arg Tyr Ile Asn
                 85                   90                   95 tca aag gct act aaa tgt cca gat gct gta gaa cct aaa gaa aga aag     336
Ser Lys Ala Thr Lys Cys Pro Asp Ala Val Glu Pro Lys Glu Arg Lys
               100                  105                  110 aat cca ttt gct aaa tat aca ttt tgg gat gtt gat cta ac              377
Asn Pro Phe Ala Lys Tyr Thr Phe Trp Asp Val Asp Leu
              115                  120                 125
```

<210> SEQ ID NO 6
<211> LENGTH: 125
<212> TYPE: PRT
<213> ORGANISM: Papillomavirus sylvilagi

<400> SEQUENCE: 6

```
Asn Gln Leu Phe Ile Thr Val Ala Asp Asn Thr Arg Asn Thr Asn Phe
1               5                   10                  15

Thr Ile Ser Val Ser Thr Glu Ala Asp Ala Gln Gln Tyr Asn Ala Ser
            20                  25                  30

Asn Ile Arg Glu Tyr Leu Arg His Val Glu Glu Tyr Gln Leu Ser Leu
        35                  40                  45

Ile Leu Gln Leu Cys Lys Leu Cys Leu Val Pro Glu Val Leu Ser Gln
    50                  55                  60

Ile Asn Ala Met Asn Ser Asn Ile Leu Glu Asp Trp Gln Leu Gly Phe
65                  70                  75                  80

Val Pro Thr Pro Asp Asn Ser Val His Asp Thr Tyr Arg Tyr Ile Asn
            85                  90                  95

Ser Lys Ala Thr Lys Cys Pro Asp Ala Val Glu Pro Lys Glu Arg Lys
        100                 105                 110

Asn Pro Phe Ala Lys Tyr Thr Phe Trp Asp Val Asp Leu
    115                 120                 125
```

<210> SEQ ID NO 7
<211> LENGTH: 380
<212> TYPE: DNA
<213> ORGANISM: Papillomavirus sylvilagi
<220> FEATURE:
<221> NAME/KEY: CDS
<222> LOCATION: (1)..(378)

<400> SEQUENCE: 7

```
aat cag atg ttt att act gta gca gat aac aca cgg aat act aat ttt     48
Asn Gln Met Phe Ile Thr Val Ala Asp Asn Thr Arg Asn Thr Asn Phe
1               5                   10                  15 acc att agt gtt acc agt gaa gat gta agc act gca caa tat aat gct    96
Thr Ile Ser Val Thr Ser Glu Asp Val Ser Thr Ala Gln Tyr Asn Ala
            20                  25                  30 caa aat att aga gag tat atg aga cat gta gaa gaa tat cag cta tct    144
Gln Asn Ile Arg Glu Tyr Met Arg His Val Glu Glu Tyr Gln Leu Ser
        35                  40                  45 ttt att ttg caa tta tgc aga gta cct tta gaa gct gag gtt tta aca    192
Phe Ile Leu Gln Leu Cys Arg Val Pro Leu Glu Ala Glu Val Leu Thr
    50                  55                  60 caa att aat gcc atg aat tct ggt ata ctt gaa aat tgg caa ctg ggt    240
Gln Ile Asn Ala Met Asn Ser Gly Ile Leu Glu Asn Trp Gln Leu Gly
```

```
                65                  70                  75                  80
ttt gta cca gct cca gat aat gca gtg cat gat aca tat cga tat tta         288
Phe Val Pro Ala Pro Asp Asn Ala Val His Asp Thr Tyr Arg Tyr Leu
                    85                  90                  95 agt tca aaa gct aca aag tgt cct gat gca gtt caa gaa aca gaa aaa         336
Ser Ser Lys Ala Thr Lys Cys Pro Asp Ala Val Gln Glu Thr Glu Lys
                100                 105                 110 gaa gac ccc ttt gga aaa tat aca ttc tgg gat gta gat cta ac             380
Glu Asp Pro Phe Gly Lys Tyr Thr Phe Trp Asp Val Asp Leu
                115                 120                 125
```

<210> SEQ ID NO 8
<211> LENGTH: 126
<212> TYPE: PRT
<213> ORGANISM: Papillomavirus sylvilagi

<400> SEQUENCE: 8

Asn Gln Met Phe Ile Thr Val Ala Asp Asn Thr Arg Asn Thr Asn Phe
1               5                   10                  15

Thr Ile Ser Val Thr Ser Glu Asp Val Ser Thr Ala Gln Tyr Asn Ala
            20                  25                  30

Gln Asn Ile Arg Glu Tyr Met Arg His Val Glu Glu Tyr Gln Leu Ser
        35                  40                  45

Phe Ile Leu Gln Leu Cys Arg Val Pro Leu Glu Ala Glu Val Leu Thr
    50                  55                  60

Gln Ile Asn Ala Met Asn Ser Gly Ile Leu Glu Asn Trp Gln Leu Gly
65                  70                  75                  80

Phe Val Pro Ala Pro Asp Asn Ala Val His Asp Thr Tyr Arg Tyr Leu
                85                  90                  95

Ser Ser Lys Ala Thr Lys Cys Pro Asp Ala Val Gln Glu Thr Glu Lys
            100                 105                 110

Glu Asp Pro Phe Gly Lys Tyr Thr Phe Trp Asp Val Asp Leu
        115                 120                 125

<210> SEQ ID NO 9
<211> LENGTH: 389
<212> TYPE: DNA
<213> ORGANISM: Papillomavirus sylvilagi

<400> SEQUENCE: 9
gatagatcta cattccaaaa gtttaatttt gcatagggt cgggccgttc ctttggagga        60
ttcttatcag gacaccttgt ggctaaagac tcaataaatc tatatgtatc gtgtatgggg      120
ttatcaggag ttggaacaaa gcccaactgc caatcctcta atatattgga gttcatggca      180
ttgatctgtg caagaacctc tgcctttaaa ggaattttac atagctgtaa atgagagaa       240
atttcgtatt cttctacatg ccttaaatat tctctgaatt gtgtggcctt gtagttttga      300
atatccttta tattccctcc ttcactatat atggatatac tgaagttagt gtttcgcgtg      360
ttgtctacaa cagtaataaa cagctgatt                                        389

<210> SEQ ID NO 10
<211> LENGTH: 129
<212> TYPE: PRT
<213> ORGANISM: Papillomavirus sylvilagi

<400> SEQUENCE: 10

Leu Asp Val Asn Trp Phe Asn Leu Lys Ala Tyr Pro Asp Pro Arg Glu
1               5                   10                  15

```
Lys Pro Pro Asn Lys Asp Pro Cys Arg Thr Ala Leu Ser Glu Ile Phe
            20                  25                  30

Arg Tyr Thr Asp His Ile Pro Asn Asp Pro Thr Pro Val Phe Gly Leu
        35                  40                  45

Gln Trp Asp Glu Leu Ile Asn Ser Asn Met Ala Asn Ile Gln Ala Leu
    50                  55                  60

Val Glu Ala Lys Leu Pro Ile Lys Cys Leu Gln Leu Ile Leu Ser Ile
65                  70                  75                  80

Glu Tyr Glu Glu Val His Arg Leu Tyr Glu Arg Phe Gln Thr Ala Lys
                85                  90                  95

Tyr Asn Gln Ile Asp Lys Ile Asn Gly Gly Glu Ser Tyr Ile Ser Ile
            100                 105                 110

Ser Phe Asn Thr Asn Arg Thr Asn Asp Val Val Thr Ile Phe Leu Gln
        115                 120                 125

Asn

<210> SEQ ID NO 11
<211> LENGTH: 422
<212> TYPE: DNA
<213> ORGANISM: Papillomavirus sylvilagi
<220> FEATURE:
<221> NAME/KEY: CDS
<222> LOCATION: (1)..(420)

<400> SEQUENCE: 11 ata gaa gac ggg gat atg gca gac att gga tat ggt aat att aat ttt        48
Ile Glu Asp Gly Asp Met Ala Asp Ile Gly Tyr Gly Asn Ile Asn Phe
1               5                   10                  15 aaa acc tta caa caa aac aga tct gat gtc agt tta gat ata gtt gac        96
Lys Thr Leu Gln Gln Asn Arg Ser Asp Val Ser Leu Asp Ile Val Asp
            20                  25                  30 gaa att tgc aag tat cct gat ttt ttg aaa atg caa aat aat att tat       144
Glu Ile Cys Lys Tyr Pro Asp Phe Leu Lys Met Gln Asn Asn Ile Tyr
        35                  40                  45 gga gat gct tgc ttt ttt tat gct aga cgg gag caa tgt tat gct aga       192
Gly Asp Ala Cys Phe Phe Tyr Ala Arg Arg Glu Gln Cys Tyr Ala Arg
    50                  55                  60 cat ttt ttt gta cga gga gga aaa cca ggt gac gac att cct gca tct       240
His Phe Phe Val Arg Gly Gly Lys Pro Gly Asp Asp Ile Pro Ala Ser
65                  70                  75                  80 cag ata gat gat ggc aat tta aaa aat gaa tat tac att cct gct gac       288
Gln Ile Asp Asp Gly Asn Leu Lys Asn Glu Tyr Tyr Ile Pro Ala Asp
                85                  90                  95 tca gcg cag cca caa aac aaa ctt gga aat tcc atg tat ttc cca act       336
Ser Ala Gln Pro Gln Asn Lys Leu Gly Asn Ser Met Tyr Phe Pro Thr
            100                 105                 110 ata agt ggt tca ttg gtg tca agt gat gcc caa tta ttt aac agg ccc       384
Ile Ser Gly Ser Leu Val Ser Ser Asp Ala Gln Leu Phe Asn Arg Pro
        115                 120                 125 ttc tgg cta caa aga gca caa ggc cac aac aac ggg at                    422
Phe Trp Leu Gln Arg Ala Gln Gly His Asn Asn Gly
    130                 135                 140

<210> SEQ ID NO 12
<211> LENGTH: 140
<212> TYPE: PRT
<213> ORGANISM: Papillomavirus sylvilagi

<400> SEQUENCE: 12

Ile Glu Asp Gly Asp Met Ala Asp Ile Gly Tyr Gly Asn Ile Asn Phe
```

-continued

```
1               5                   10                  15
Lys Thr Leu Gln Gln Asn Arg Ser Asp Val Ser Leu Asp Ile Val Asp
            20                  25              30

Glu Ile Cys Lys Tyr Pro Asp Phe Leu Lys Met Gln Asn Asn Ile Tyr
        35                  40              45

Gly Asp Ala Cys Phe Phe Tyr Ala Arg Arg Glu Gln Cys Tyr Ala Arg
    50                  55                  60

His Phe Phe Val Arg Gly Gly Lys Pro Gly Asp Asp Ile Pro Ala Ser
65                  70              75                      80

Gln Ile Asp Asp Gly Asn Leu Lys Asn Glu Tyr Tyr Ile Pro Ala Asp
            85                  90              95

Ser Ala Gln Pro Gln Asn Lys Leu Gly Asn Ser Met Tyr Phe Pro Thr
            100                 105             110

Ile Ser Gly Ser Leu Val Ser Ser Asp Ala Gln Leu Phe Asn Arg Pro
        115                 120                 125

Phe Trp Leu Gln Arg Ala Gln Gly His Asn Asn Gly
130                 135             140
```

We claim:

1. An isolated polynucleotide having:
   (a) a nucleotide sequence encoding the peptide of SEQ ID NO:2, SEQ ID NO:4, or SEQ ID NO:6;
   (b) a nucleotide sequence hybridizing to the nucleotide sequence of SEQ ID NO:3, or SEQ ID NO:5; or
   (c) the complement of (a) or (b);
   wherein the polynucleotide has a homology of at least 90% to the nucleotide sequence of SEQ ID NO:3, or SEQ ID NO:5.

2. An isolated polynucleotide encoding a peptide of a papilloma virus major capsid protein, wherein the said polynucleotide has been obtained using the following steps:
   (a) incubating total DNA isolated from a biopsy of epithelial neoplasm with a nucleic acid having at least a portion of the nucleotide sequence of SEQ ID NO:3, or SEQ ID NO:5, under a condition that allows hybridization of a polynucleotide derived from a papilloma virus genome included in the total DNA to said nucleotide sequence of SEQ ID NO:3, or SEQ ID NO:5; and
   (b) identifying and isolating a polynucleotide that hybridizes to the nucleotide sequence of SEQ ID NO:3, or SEQ ID NO:5 in step (a);
      wherein the polynucleotide has a homology of at least 90% to the nucleotide sequence of SEQ ID NO:3, or SEQ ID NO:5.

3. An isolated polynucleotide, having (a) a nucleic acid encoding a peptide comprising the amino acid sequence of SEQ ID NO:2, SEQ ID NO:4, or SEQ ID NO:6, or (b) the complement of (a).

4. An isolated polynucleotide, wherein the polynucleotide consists essentially of the nucleotide sequence of SEQ ID NO: 1, SEQ ID NO:3, or SEQ ID NO:5, or the complement thereof.

5. A plasmid comprising the polynucleotide of claim 1 or 2.

6. A plasmid comprising the polynucleotide of claim 3.

7. An expression vector comprising the polynucleotide of claim 1 or 2.

8. An expression vector comprising the polynucleotide of claim 3.

9. A host cell comprising the plasmid of claim 5.

10. A host cell comprising the plasmid of claim 6.

11. A host cell comprising the expression vector of claim 7.

12. A host cell comprising the expression vector of claim 8.

13. A composition comprising the polynucleotide of claim 1, 2, 3, or 4 as reagent for diagnosis and a diagnostically acceptable carrier.

14. A method of producing a peptide of a papilloma virus major capsid protein, comprising cultivating the host cell of claim 11 under suitable conditions.

15. A method of producing a peptide of a papilloma virus major capsid protein, comprising cultivating the host cell of claim 12 under suitable conditions.

16. A method of detecting a papilloma virus DNA, comprising:
   (a) hybridizing under stringent conditions at least a portion of the polynucleotide of claim 1, 2, 3, or 4 to a DNA sample; and
   (b) identifying papilloma virus in said DNA sample by detecting a hybridization signal.

* * * * *

UNITED STATES PATENT AND TRADEMARK OFFICE
CERTIFICATE OF CORRECTION

PATENT NO. : 6,589,532 B1
DATED : August 13, 2003
INVENTOR(S) : Ethel-Michele De Villiers-Zur et al.

It is certified that error appears in the above-identified patent and that said Letters Patent is hereby corrected as shown below:

<u>Title page,</u>
Item [73], Assignee should read:
-- Deutsches Krebsforschungszentrum Stiftung des Offentlichen Rechts, Heidelberg (DE) --
Item [86], the § 371 (c)(1), (2), (4) Date should read:
-- June 12, 2001 --

Signed and Sealed this

Second Day of December, 2003

JAMES E. ROGAN
*Director of the United States Patent and Trademark Office*